US 6,480,010 B2
United States Patent
Ikuta et al.

(12)
(10) Patent No.: US 6,480,010 B2
(45) Date of Patent: Nov. 12, 2002

(54) METHOD OF INSPECTING PIEZOELECTRIC CERAMIC DEVICE

(75) Inventors: Masato Ikuta, Omihachiman (JP); Toshinari Tabata, Otsu (JP); Masao Nishimura, Shiga-ken (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 0 days.

(21) Appl. No.: 09/746,324

(22) Filed: Dec. 22, 2000

(65) Prior Publication Data

US 2002/0024346 A1 Feb. 28, 2002

(30) Foreign Application Priority Data

Dec. 24, 1999 (JP) ............................. 11-365929
Dec. 4, 2000 (JP) ........................ 2000-369009

(51) Int. Cl.[7] .............................................. G01R 29/22
(52) U.S. Cl. ....................................... 324/727; 324/765
(58) Field of Search ................................ 324/727, 765, 324/310

(56) References Cited

U.S. PATENT DOCUMENTS 4,653,855 A * 3/1987 Birnbach ..................... 324/310

FOREIGN PATENT DOCUMENTS

JP      6-3305      1/1994

OTHER PUBLICATIONS

"Noncontact Holographic Thermal Imaging", IBM Technical Disclosure Bullentin, vol. 29, No. 11, (Apr. 1, 1987), pp. 4876–7879.*

* cited by examiner

Primary Examiner—Christine K. Oda
(74) Attorney, Agent, or Firm—Keating & Bennett, LLP

(57) ABSTRACT

A piezoelectric ceramic device is heated so that the temperature is increased to a temperature in the vicinity of the maximum temperature at which the device, when the temperature is returned to ordinary temperature, is returned to substantially the same piezoelectric characteristic before heating. In the state that the piezoelectric ceramic device is heated, and the temperature is increased, at least one of the piezoelectric phase characteristic and the impedance characteristic of the piezoelectric ceramic device is measured. The measurement is compared with a standard characteristic, whereby an internal defect of the piezoelectric ceramic device is detected, based on results of the comparison. For the heating and temperature-increasing, and the measuring, a high frequency measurement signal having a power level that is higher than the rated level of the piezoelectric ceramic device is applied, and simultaneously with the piezoelectric ceramic device itself being dielectric-heated by the application of the high frequency signal, at least one of the piezoelectric phase characteristic and the impedance characteristic is measured.

20 Claims, 6 Drawing Sheets

θ characteristic while the temperature is increasing

θ characteristic when the high level signal is applied

METHOD OF INSPECTING PIEZOELECTRIC CERAMIC DEVICE

BACKGROUND OF THE INVENTION

1. Field of the Invention

The present invention relates to a method of non-destructively inspecting internal defects such as microcracks or other defects which may occur in a piezoelectric ceramic device such as an oscillator, a filter, or other such device, which defects affect the qualities and characteristics of the piezoelectric ceramic device.

2. Description of the Related Art

In a conventional method of non-destructively inspecting an internal defect of a piezoelectric ceramic device, the impedance and/or phase characteristic of a piezoelectric ceramic device is measured, the curve pattern representing the characteristic is compared with a standard curve pattern, and if the curve patterns are different from each other, it is judged that microcracks are present in the piezoelectric ceramic substrate, as described in Japanese Unexamined Patent Application Publication No. 6-3305.

According to such an inspection method, automatic judgement is possible. Thus, advantageously, judgement as to whether lots of piezoelectric ceramic devices are non-defective or defective can be performed quickly and efficiently. Moreover, the inspection accuracy is high, since the inspection is not visually performed.

According to the above-described inspection method, an electrical characteristic is measured at an ordinary temperature and compared with a standard characteristic. However, there are many cases in which a difference between non-defective components and defective components is small or is non-existent at ordinary temperatures. Thus, using the above-described inspection method, it is impossible to detect an internal defect such as microcracks or other defects completely.

In one example, each of a plurality of ceramic oscillators (oscillation frequency: 25 MHz) was incorporated in an oscillation circuit, the oscillator was placed in an atmosphere at a temperature of 200° C. while the oscillator was being oscillated, and then, characteristics of the oscillation voltage were measured. FIG. 1 shows the measurement results. The characteristics of these oscillators are not different at ordinary temperature.

As seen in FIG. 1, the oscillation voltages are slightly decreased with the increase of the temperature. Some of the oscillators (NG) are decreased to about OV, and the oscillation is stopped. For the other oscillators (G), the oscillation is not stopped even at 200° C. or higher.

These oscillators were opened, and the internal devices were observed with a microscope. For the oscillators (NG) that had their oscillation stopped at a low temperature, it was determined that microcracks were formed inside of the devices. Accordingly, it has been discovered that some oscillators that normally oscillate and exhibit normal characteristics at ordinary temperatures have microcracks inside thereof, and such an internal defect can be detected by measuring the characteristic of oscillators while they are heated according to preferred embodiments of the present invention described below.

SUMMARY OF THE INVENTION

In order to overcome the problems described above, preferred embodiments of the present invention provide a method of inspecting a piezoelectric ceramic device in which an internal defect, which may be undetectable at ordinary temperature, can be accurately and reliably detected non-destructively.

In addition, preferred embodiments of the present invention provide a method of inspecting a piezoelectric ceramic device in which an internal defect can be detected at high speed using a simple instrument.

According to a preferred embodiment of the present invention, a method of inspecting a piezoelectric ceramic device includes the steps of heating and increasing the temperature of a piezoelectric ceramic device to an increased temperature that is in the vicinity of a maximum temperature at which the piezoelectric ceramic device, when the temperature of the device is returned to ordinary temperature, is returned to substantially the same piezoelectric characteristic as that before heating, measuring at least one of the piezoelectric phase characteristic and the impedance characteristic of the piezoelectric ceramic device while the device is heated and the temperature thereof is increased, comparing at least one of the measured piezoelectric phase characteristic and the measured impedance characteristic with a standard characteristic, and detecting the presence or absence of an internal defect of the piezoelectric ceramic device based on results of the step of comparing.

In this preferred embodiment of the present invention, first, the piezoelectric ceramic device is heated so that the temperature thereof is increased.

Next, when at least one of the phase characteristic and the impedance characteristic of the piezoelectric ceramic device in a state of heating and increasing the temperature, a large change is shown with the piezoelectric ceramic device having internal defects in accordance with the temperature increase, such large change is not shown in the normal temperature. Then, one of the measured phase characteristic and the measured impedance characteristic is compared with the standard characteristic. The standard characteristic may be attained from the phase characteristic or the impedance characteristic of the good piezoelectric ceramic device (without internal defects), for example.

As a result of the above-described comparison, if the measured characteristic is different from the standard characteristic so as to exceed a predetermined range of the characteristic, it is judged that the piezoelectric ceramic device has an internal defect.

In addition, according to preferred embodiments of the present invention, not only microcracks but also foreign matters stuck to an electrode can be detected.

It would be preferable to set the increased temperature of heating to the temperature which is in the vicinity of the maximum temperature in which the piezoelectric characteristic of the piezoelectric ceramic device returns to substantially the same as that of before heating when the piezoelectric ceramic device is back to the normal temperature after heating. The internal defects, which cannot be inspected in the normal temperature, can be securely inspected by heating at as high temperature as possible as long as the piezoelectric characteristic can come back. When the piezoelectric ceramic device is heated at higher temperature than the above described temperature, the piezoelectric characteristic of the piezoelectric ceramic device itself is changed non-reversibly, thereby being not preferable.

Preferably, as the phase characteristic to be measured, a maximum phase angle $\theta_{max}$ is used. At ordinary temperature, the piezoelectric ceramic device presents the phase characteristic shown by solid line $P_1$ in FIG. 2. At a higher temperature, the phase is reduced as shown by broken line $P_2$. The larger the internal defect of the piezoelectric ceramic device becomes, the more the amount of phase reduction increases. Preferably, an internal defect is judged by utilization of the phase reduction.

FIG. 3 shows the results obtained when devices NG having an internal defect and devices G having no internal defect are heated in the same manner, and the maximum phase angles in the vicinity of the oscillation frequency $f_{osc}$ are measured. As seen in FIG. 3, the devices NG having an internal defect present a larger reduction in maximum phase angle, as compared with the devices G having no internal defect. Thus, it can be seen that there is a correlation between the internal defect and the maximum phase angle.

For the devices NG having an internal defect, the phases are not more than about 60°. On the other hand, for the devices G having no internal defect, the phases are not less than about 70°. In the case of these devices, it can be securely detected whether an internal defect is present or not by setting the raised temperature for use in judgement of a non-defective or a defective at about 150° or higher, and moreover, setting the maximum phase angle as a threshold for the judgement of whether a device is non-defective or defective.

Preferably, as the impedance characteristic to be measured, the difference Za–Zr between an antiresonance impedance Za and a resonance impedance Zr is used. At ordinary temperature, the impedance characteristic can be shown as indicated by solid line $I_1$ in FIG. 2. At a higher temperature, both of the antiresonance and resonance points are shifted to the higher frequency side, and moreover, the impedance difference Za–Zr is reduced. Preferably, an internal defect is judged by use of this characteristic.

In addition to Za–Zr, values per se of Za and Zr, a frequency change ratio (dZa/df) at an antifrequency point, a frequency change ratio (dzr/df) at a resonance point, an oscillation frequency $f_{osc}$, an anti-resonance frequency fa, and a resonance frequency fr may be used.

It should be noted that the phase characteristic and the impedance characteristic to be measured are not limited to the above ones. Other suitable measurements may also be used.

Referring to a method of heating the piezoelectric ceramic device to increase the temperature, for example, the device is placed in a high temperature atmosphere, or externally heated via a heater. However, according to these methods, it takes at least several seconds to increase the temperature of the device. The efficiency is very low, and moreover, large-scale equipment is required for heating. Accordingly, preferably, the heating and temperature-raising is performed by that a high frequency measurement signal having a level that is higher than the rated level of the piezoelectric ceramic device is applied to the piezoelectric ceramic device with the piezoelectric ceramic device itself being dielectric-heated via application of the high frequency signal, and the measuring step is performed by that at least one of the phase characteristic and the impedance characteristic of the piezoelectric ceramic device in accordance with the application of the high frequency signal is measured.

That is, the inventors of the present invention discovered that by increasing the power level of the measurement signal, the device is quickly heated via dielectric heating. In this case, if the power level is excessively high, the temperature becomes too high, resulting in deterioration of the characteristics of the device. In such a case of overheating, the piezoelectric ceramic device, when the temperature is returned to ordinary temperature, cannot be returned to the piezoelectric characteristic before heating. For this reason, it is preferable to select a high frequency measurement signal having a level that is higher than the rated level of the device and is the possible highest level in the range of temperature where the piezoelectric characteristic can be returned to the characteristic existing before the device was heated. Moreover, devices having different oscillation frequencies have different thicknesses. Accordingly, it is necessary to select the power level corresponding to such differences.

As described above, the heating and temperature-increasing step and the measuring step can be performed simultaneously using the same equipment. As a result, the heating and measuring time is greatly reduced. Moreover, it is only necessary to increase and control the power level of an existing measuring instrument. Thus, these steps can be performed using very simple and relatively inexpensive equipment.

FIG. 4 shows increasing-temperature curves (calculation values) obtained by heating the device by dielectric heating. The respective curves are obtained by changing stepwise the power level from about 30 dBm to about 40 dBm. As seen in FIG. 4, when a time period of about 400 msec. elapses from the start of application of heat, the temperature nearly reaches the maximum temperature.

As described above, when the device is heated by dielectric heating, the temperature can be increased to a target temperature in about several hundred seconds. Thus, the temperature-increasing time is significantly reduced, and also, the time required for detection of an internal defect is greatly reduced. Moreover, advantageously, the temperature of the device can be quickly returned to its initial value, since the heating is local and spontaneous.

According to the present invention, the piezoelectric ceramic device is heated from inside using the dielectric heating by applying the high frequency signal of a high level. It requires about 400 msec. for inspecting the defects. Then, at the same time of this internal heating, when the piezoelectric ceramic device is heated externally, the measuring time can be shortened further, because the piezoelectric ceramic device can be heated to the predetermined temperature quickly. So, it is preferable to combine the internal heating and the external heating in order to reduce the measuring time.

In the internal heating (dielectric heating), the piezoelectric ceramic device generates heat at portions of vibration electrodes and the generated heat is transmitted to the outer peripheral portions. On the other hand, in the external heating, the generated heat of the piezoelectric ceramic device is transmitted from the outer peripheral portions to the inside. Thus, when the internal heating and the external heating are used at the same time, not only that the measuring time can be reduced, but also that the piezoelectric ceramic device can be heated to increase the temperature uniformly over the device.

As a method of the external heating, there may be a method of using the convection, a method of using the radient heat, a method of using the transmitting heat, etc. In order to heat and increase the temperature in a short period and with a simple equipment, the transmitting heat method is preferable.

When the phase characteristic and the impedance characteristic of the piezoelectric ceramic device in the state of being heated are measured, the defects which could not be inspected at the normal temperature can be inspected.

However, there are some piezoelectric ceramic device whose phase characteristic goes beyond the standard value area in accordance with the temperature increase and goes back in the standard value area after the internal defects are inspected when the temperature is further increased. Such piezoelectric ceramic devices are also defect products.

FIG. 5 shows the relationship between the temperature and the maximum phase angle θmax in the heating process when the piezoelectric ceramic device is heated externally.

In FIG. 5, G denotes a good average phase characteristic. NG1 and NG2 are phase characteristics of the defect products having internal defects. In the cases of NG1 and NG2, the phase characteristics go away from the standard characteristic (the characteristic of G) at a predetermined temperature (70 or 120), and the internal defects can be inspected. However, when the temperature is increased further, the phase characteristics thereof do not differ from the standard characteristic, the internal defects cannot be inspected.

FIG. 6 shows the relationship between the lapse time and the maximum phase angle θmax, when the piezoelectric ceramic device is dielectric heated.

As shown from FIG. 6, the defect is inspected at the lapse time of about 150 msec. and after that the characteristic comes back to the normal value in case of NG1. In NG2, the characteristic is normal before the lapse time of 300 msec. but after that the defect is inspected.

Note here that the piezoelectric ceramic devices of NG1 and NG2 in FIG. 6 are the same as NG1 and NG2 in FIG. 5.

Further, the reason why the state of the defects of NG1 is different from that of NG2 is assumed to be due to the differences in generating positions of micro cracks.

In this way, when the inspection is performed only at a predetermined temperature and at a predetermined lapse time, a defect of the piezoelectric ceramic device whose characteristic returns to the standard value cannot be inspected.

So, according to the present invention, at least one of the phase characteristic and the impedance characteristic of the piezoelectric ceramic device is measured at a plurality of different temperature inside the device. When the measurement is performed at the plurality of temperature values, the internal defects of the piezoelectric ceramic device, whose characteristic goes away from the standard value and returns to the standard value, can be inspected.

As for the temperature interval of measuring, referring to FIG. 5, it is preferable to set the interval less than 50.

According to the present invention, the characteristics are measured at different temperature values inside the piezoelectric ceramic device. However, when the piezoelectric ceramic device is internally heated by applying the high frequency signal, it would be difficult to inspect the internal temperature of the piezoelectric ceramic device directly. In such a case, the characteristics are measured at a plurality of lapse times after applying the high frequency signal which is higher than the standard level.

When higher level high frequency signal is applied, as shown in FIG. 4, the internal temperature of the device increases in accordance with the lapse time. Therefore, when the characteristics are measured at a plurality of lapse times, the internal defects of the piezoelectric ceramic device, whose defects can be only in a certain range of temperature, can be inspected securely. Further, when the measuring timing is determined by the lapse time, it is not necessary to inspect the internal temperature of the device, thereby simplifying the measurement.

Other features, elements, characteristics and advantages of the present invention will become more apparent from the detailed description of preferred embodiments of the present invention with reference to the attached drawings.

DETAILED DESCRIPTION OF PREFERRED EMBODIMENTS

Figure 5:
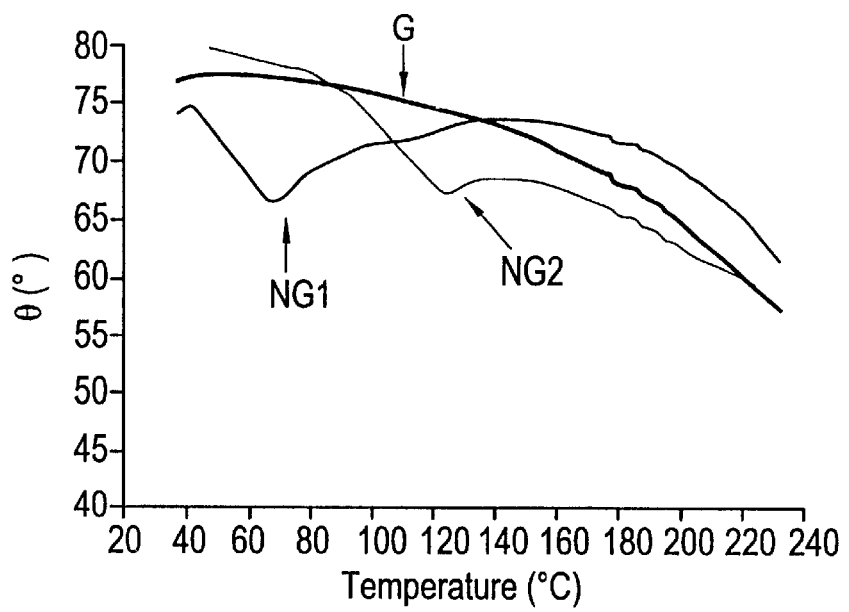
FIG. 5 is a graph showing the variation of maximum phase angles of the devices with and without an internal defect, when the temperature is increased due to the external heating.
Figure 7:
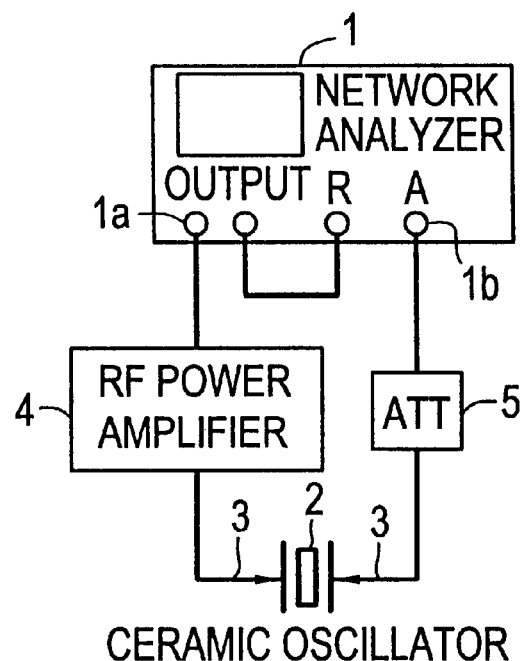
FIG. 7 shows the configuration of an instrument for carrying out the inspection method of a preferred embodiment of the present invention.

FIG. 7 shows an example of an inspection instrument for use in performing the inspection method of preferred embodiments of the present invention. In FIG. 5, as the piezoelectric ceramic device, a ceramic oscillator 2 is preferably used.

A network analyzer 1 is shown which measures and analyzes an electrical characteristic as a function of frequency of the ceramic oscillator 2. A high frequency measurement signal is output from an output terminal 1a of a sine wave sweep oscillator contained in the instrument, and is applied to the ceramic oscillator 2 via measurement terminals 3a and 3b, whereby the phase or impedance characteristic of the ceramic oscillator is measured. In FIG. 7, the inspection instrument corresponding to one channel is shown. However, the inspection instrument can be adapted to a plurality of channels.

An RF power amplifier 4 is connected between the output terminal 1a of the network analyzer 1 and the measurement terminal 3a. Amplified power is supplied to the ceramic oscillator 2 via the measurement terminal 3a. More specifically, a signal level ordinarily used for measurement of the impedance characteristic is about 0 dBm. In preferred embodiments of the present invention, the output level of the power amplifier 4 is preferably about 20 dBm to about 40 dBm. A signal flowing through the ceramic oscillator 2 is transmitted from the measurement terminal 3b to an attenuator 5, and is attenuated to the original power via the attenuator 5, and input to an input terminal 1b of the network analyzer 1.

Figure 4:
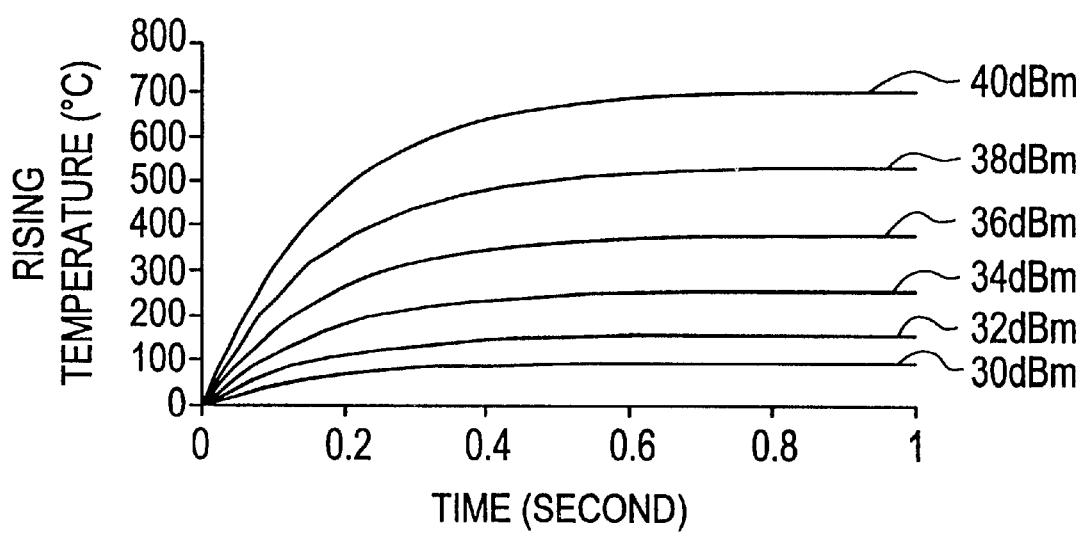
FIG. 4 is a graph showing the time-dependent changes caused when increasing the temperature of devices via dielectric heating.

The network analyzer 1 applies a high frequency measurement signal to one ceramic oscillator 2 for approximately several hundred ms. At least one of the impedance characteristic and the phase characteristic are measured while the ceramic oscillator 2 is heated to a predetermined temperature by dielectric heating. For example, in the case in which the ceramic oscillator 2 is heated to approximately 200° C., the temperature reaches approximately 200° C. in about 200 ms when the output level of the ceramic oscillator 2 is about 34 dBm, as seen in FIG. 4. The phase characteristic is a frequency characteristic of the phase differences (phase angles) that are the averages of the measurements of phase differences between currents and voltages. The maximum phase angle $\theta_{max}$ in the vicinity of, e.g., an oscillation frequency $f_{osc}$ is determined, based on the phase characteristic. If the maximum phase angle $\theta_{max}$ is not less than a standard value, the device is judged to be non-defective. If the maximum phase angle $\theta_{max}$ is lower than the standard value, the device is judged to be a defective device that has an internal defect which defect was undetectable with conventional methods.

Figure 1:
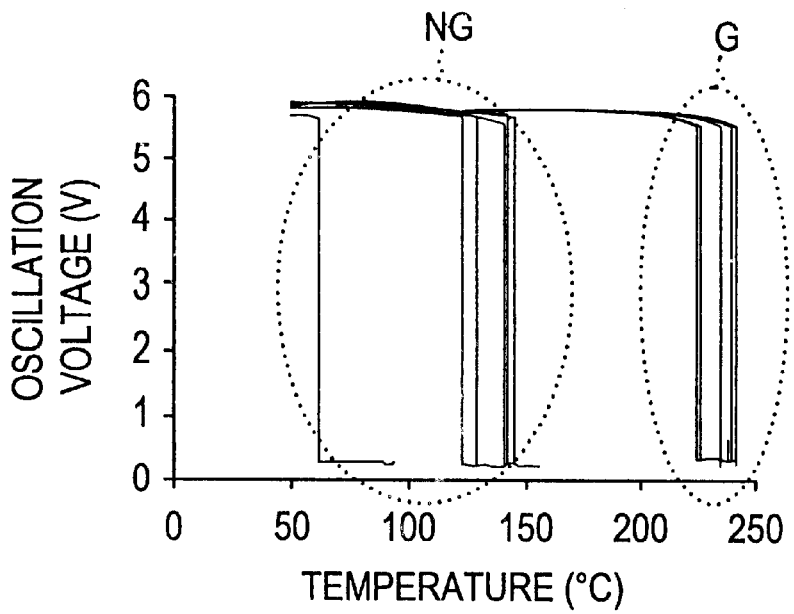
FIG. 1 is a graph showing the changes in oscillation voltage of oscillators with and without an internal defect, caused when the temperatures of the oscillators are being increased.
Figure 2:
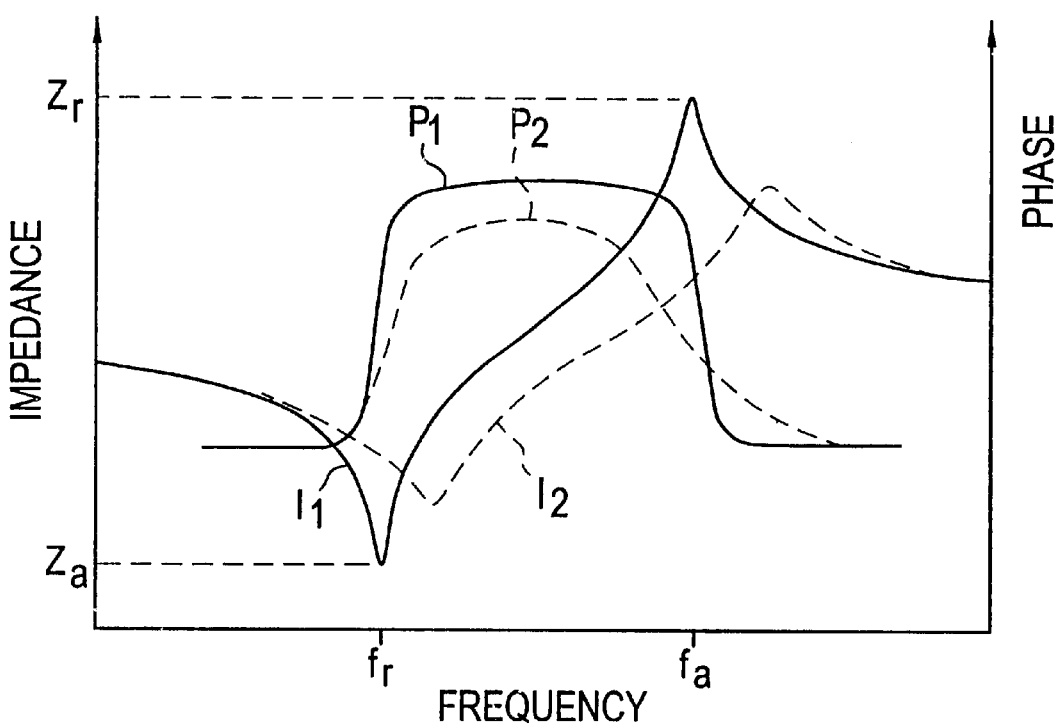
FIG. 2 is a graph showing the impedance and phase characteristics of a-ceramic oscillator.
Figure 3:
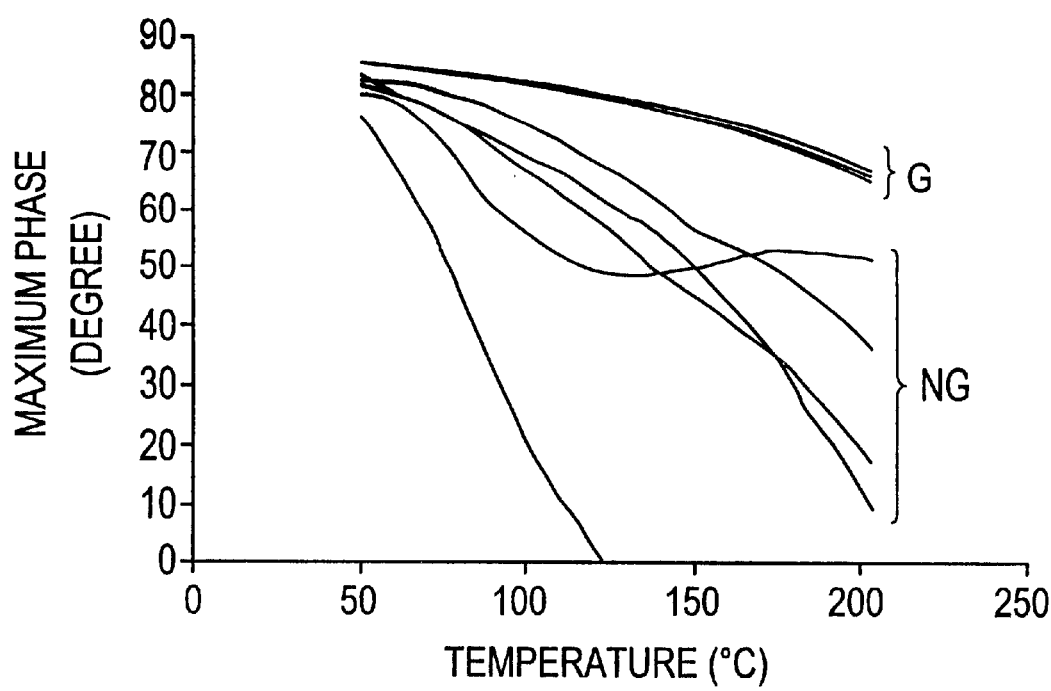
FIG. 3 is a graph showing the changes in maximum phase angle of devices with and without an internal defect, caused when the temperatures of the devices are being increased.
Figure 8:
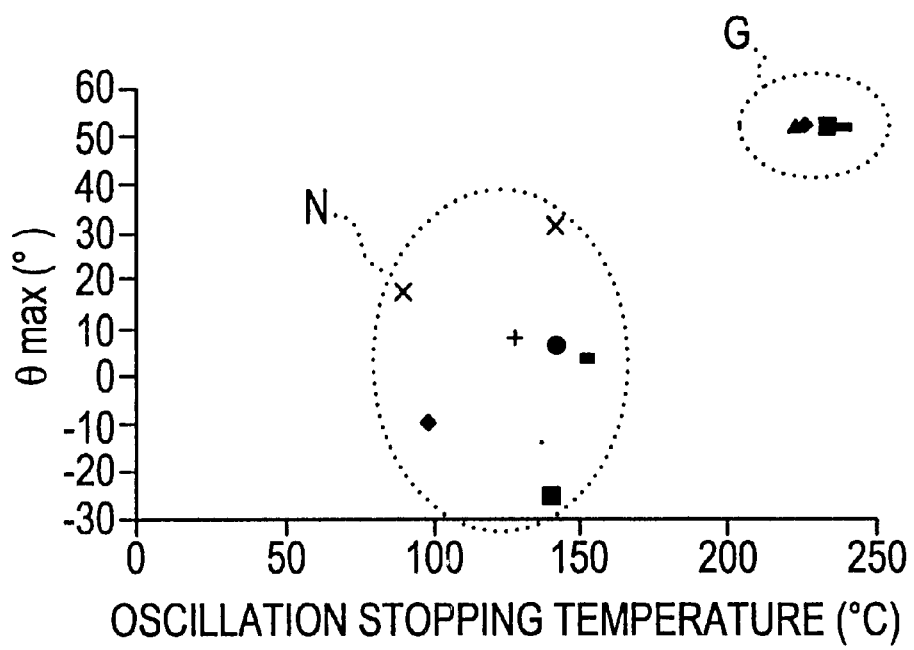
FIG. 8 is a graph showing a correlation between the oscillation stopping temperatures of devices with and without an internal defect, and the maximum phase angles of the devices when they are dielectric-heated caused by application of a high level signal.

FIG. 8 illustrates a relationship between the $\theta_{max}$ values in the vicinity of $f_{osc}$ obtained when a measurement signal at about 34 dBm is applied to the device of FIG. 1, and oscillation-stopping temperatures. By making reference to FIG. 1, it is understood that the standard value may be about 40 to about 50.

Figure 6:
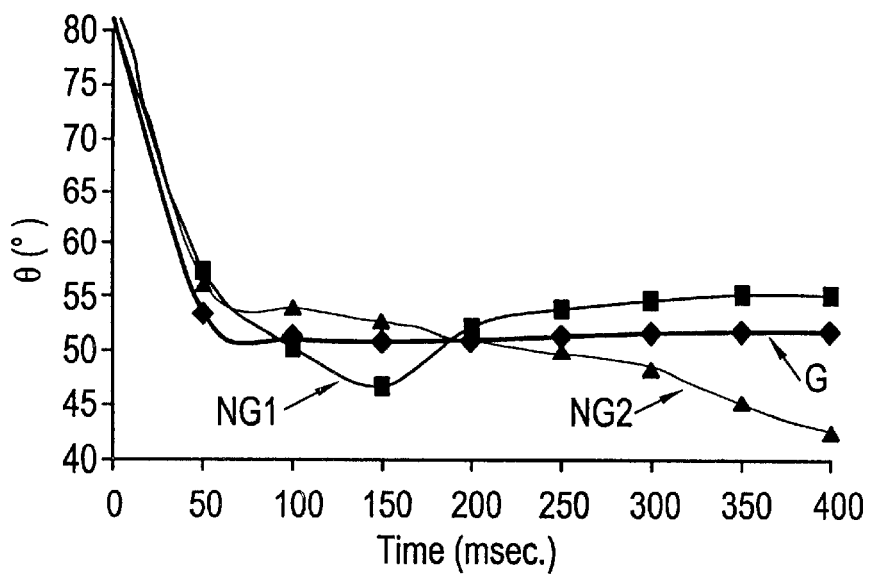
FIG. 6 is a graph showing the variation of maximum phase angles of the devices with and without an internal defect, when the temperature is increased due to the dielectric heating.

As explained referring to FIG. 5 and FIG. 6, there are some piezoelectric ceramic devices, whose phase characteristic or impedance characteristic goes away from the standard value range in accordance with the temperature increase and returns to the standard value range later. A method of inspecting such a piezoelectric ceramic device is shown in FIG. 9.

Figure 9:
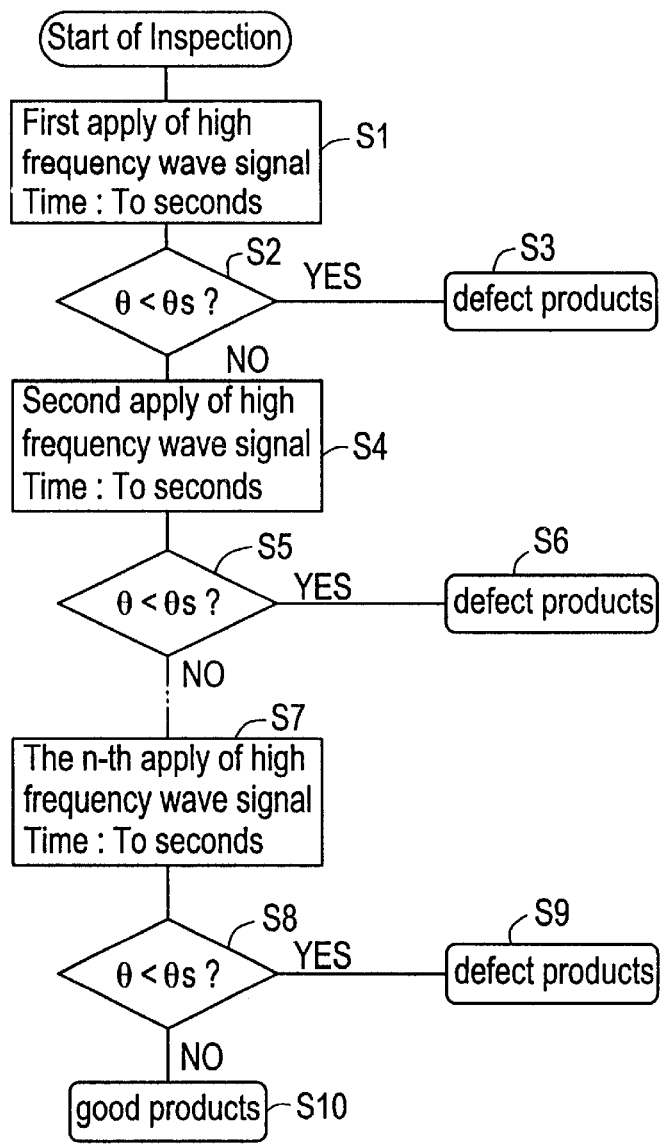
FIG. 9 is a flow chart showing a method for discriminating whether the devices are good or not by inspecting several times.

In FIG. 9, when the measurement is started, a first high frequency measurement signal is applied to the piezoelectric ceramic device for $T_0$ seconds (STEP S1). Due to this, since the temperature of the piezoelectric ceramic device is increased by the dielectric heating, the maximum phase angle θ and the standard value θs are compared after $T_0$ seconds (STEP S2). When the comparing result is $\theta<\theta_s$, it is determined that it is a defect product (STEP S3).

In STEP S2, when the comparing result is $6\theta\ \theta_s$, a second high frequency measurement signal is applied to the piezoelectric device for Tseconds (STEP S4).

Due to this, since the piezoelectric ceramic device is further heated, the maximum phase angle θ and the standard value $\theta_s$ are compared after $T_0$ seconds (STEP S5). When the comparing result is $\theta<\theta_s$, it is determined that it is a defect product (STEP S6). After that, the same steps are repeated.

Lastly, the n-th high frequency measurement signal is applied to the piezoelectric ceramic device for To seconds (STEP S7). At this point, since the piezoelectric ceramic device is heated approximately to the maximum temperature, the maximum phase angle θ and the standard value θs are compared after $T_0$ seconds (STEP S8). Here, when the comparing result is $\theta<\theta_s$, it is determined to have a defect (STEP S9). When the comparing result is θ $\theta_s$, it is determined that there is no defects (STEP S10).

Note that there is no stop period while the first to n-th high frequency signal are applied, the signal is applied to the piezoelectric ceramic device continuously.

In FIG. 9, although the applying time (inspecting time) $T_0$ of the first to n-th high frequency signal is constant, the applying time $T_0$ can be changed arbitrarily. Especially, while the defects are not appeared frequently, the applying time $T_0$ may be long. Further, the defects are appeared frequently, the applying time $T_0$ may be short.

In addition, when the inspecting time $T_0$ is short, the inspection result is substantially the same as in the continuous inspection. Therefore, the defects can be inspected securely even though the phase angle of the piezoelectric ceramic device is away from the standard value at any temperature values.

Figure 10:
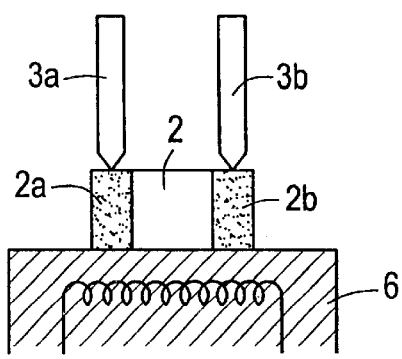
FIG. 10 is a view showing an inspecting method when both the internal heating and the external heating are performed.

FIG. 10 shows a second embodiment of the inspecting device for performing the method of inspection according to the present invention. In this embodiment, both the internal heating by dielectric heating and the external heating are used in order to shorten the measuring time.

FIG. 10 shows the piezoelectric ceramic device 2 in the state that the electrodes 2a and 2b are contacted with a pair of measuring terminals 3a and 3b. As in FIG. 7, one (3a) of the measuring terminals is connected to the RF power amplifier 4, and the other measuring terminal 3b is connected to the attenuator 5.

The piezoelectric ceramic device 2 is absorbed with the heat transmitting plate 6 by air absorption (not shown). Since the heat transmitting plate 6 is heated to the predetermined temperature.

When the higher level high frequency signal is applied to the piezoelectric ceramic device 2 via measuring terminals 3a and 3b, the device 2 is heated and the device 2 is externally heated by the heat transmitting plate 6. In this state, the phase angle or the impedance can be measured by the network analyzer (shown in FIG. 7) connected to the measuring terminals 3a and 3b.

Figure 11:
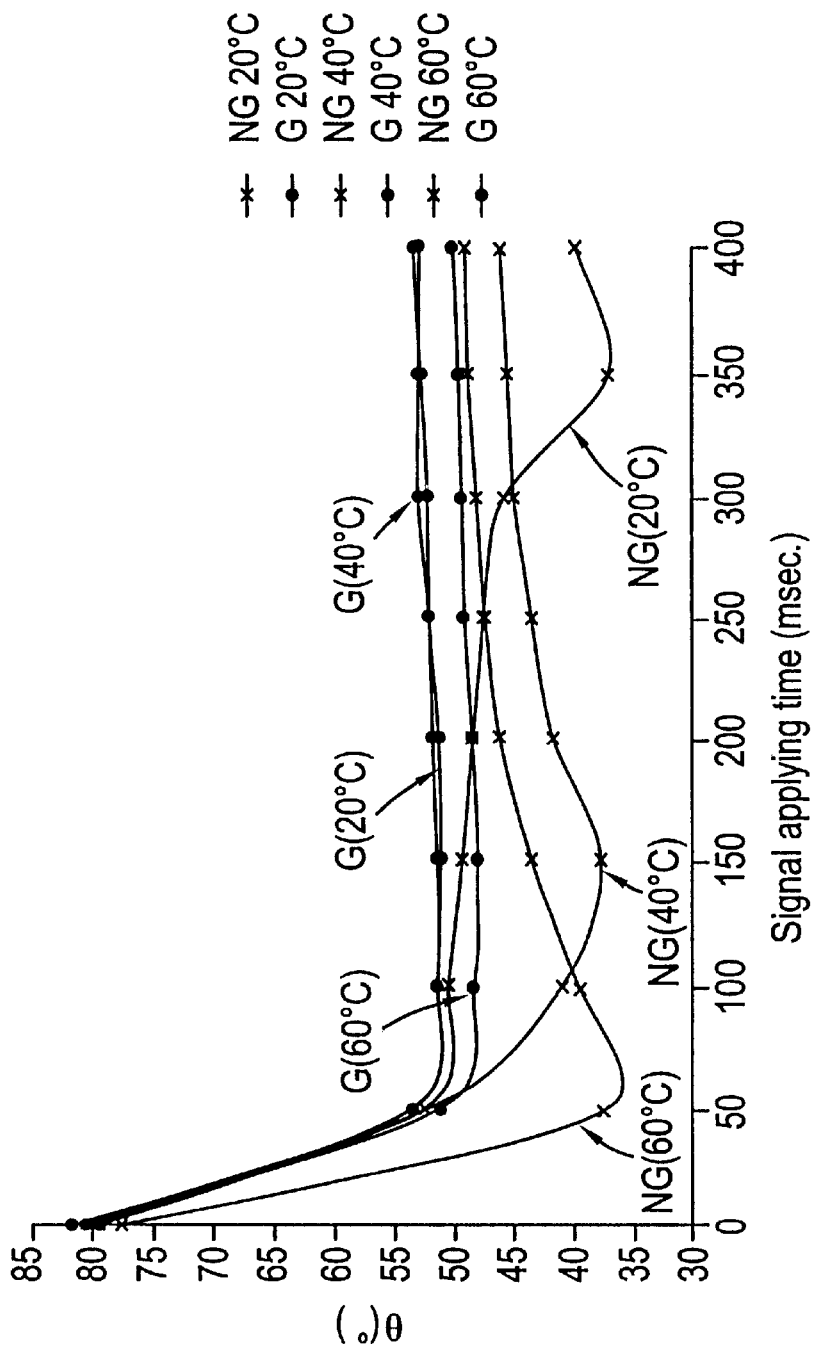
FIG. 11 is a graph showing the variation of the phase angles in relation to time, of the devices with and without defects when both the internal heating and the external heating are performed.

FIG. 11 shows an advantage of time reduction when both the internal heating and the external heating are performed. Namely, under the atmosphere temperature values of 20, 40, and 60, a high frequency signal (signal level is 0.9W) is applied to good products G and defect products NG in the dielectric heating to measure the phase characteristic.

As for the good products G and defect products NG, the same piezoelectric devices are used, respectively.

As clearly shown in FIG. 11, when the atmosphere temperature increases, inspecting time of defects can be shortened. Specifically, when the temperature is 20, the defects appear at 350 msec. In case of 40, the defects appear at 100 to 150 msec. When the temperature is 60, the defects appear at 50 msec.

In this way, when both the dielectric heating and the external heating are performed, measuring time can be shortened, compared with the case when only the internal heating is performed.

The present invention is not limited to the above-described examples of preferred embodiments.

In an embodiment of FIG. 9, the measurement was performed several times by comparing the phase angle with the standard value at the time of $T_0$ by performing the dielectric heating. However, when the internal temperature of the piezoelectric ceramic device can be measured, the measurement can be performed several times by measuring the phase angles in different temperature values and by comparing these phase angles with the standard value.

In the above examples, an internal defect is judged by comparing the maximum phase angle obtained when a piezoelectric ceramic device is heated with the increased temperature, with the standard value. The internal defect may be judged based on impedances Za and Zr or based on both of the phase angle and the impedances.

Furthermore, as a method of the external heating, a method of using the transmitting heat by the contact with a heat transmitting plate is used. But the piezoelectric ceramic device may be placed in a liquid or in an atmosphere where the temperature is controlled, or a heating wire and a radiant heat may be used.

The piezoelectric ceramic device inspected by the methods of preferred embodiments of the present invention is not limited to a ceramic oscillator, and may be a ceramic filter, a discriminator, a trap filter, and other suitable electronic component.

Moreover, an internal defect can be detected using the methods of preferred embodiments of the present invention regardless of different vibration modes such as thickness extensional vibration, thickness shear vibration, area vibration, and so forth.

As is clear from the above-description, according to preferred embodiments of the present invention, a piezoelectric ceramic device is heated, and while the device is at the maximum temperature at least one of the piezoelectric characteristic and the impedance characteristic of the piezoelectric ceramic device is measured, and the measurement is compared with a standard characteristic, whereby it is judged whether the piezoelectric ceramic device has an internal defect or not. Accordingly, an internal defect, even if it cannot be detected at ordinary temperature, can be accurately and reliably detected non-destructively.

Preferably, a high frequency measurement signal having a level that is higher than the rated level of the piezoelectric ceramic device is applied, and simultaneously with the piezoelectric ceramic device being dielectric-heated by the application of the high frequency signal, at least one of the phase characteristic and the impedance characteristic of the piezoelectric ceramic device is measured. Therefore, the time required for the heating and temperature-increasing, and the measuring is considerably reduced. In addition, the heating, temperature-increasing and the measuring can be performed using a simple instrument.

According to the present invention, when both the internal heating (dielectric heating) and the external heating are performed to the piezoelectric ceramic device, the internal defects of the piezoelectric ceramic device can be inspected in a shorter time.

As in the present invention, when the phase characteristic or the impedance characteristic of the piezoelectric ceramic device is measured at a plurality of temperature values inside the piezoelectric ceramic device, such a piezoelectric ceramic device, whose characteristic goes away from the standard characteristic and returns to the standard characteristic, can be securely inspected.

When the characteristic is measured at a plurality of lapse times after applying the high frequency signal to the piezoelectric ceramic device, such a piezoelectric ceramic device, whose characteristic goes away from the standard characteristic and returns to the standard characteristic, can be inspected. Further, since the measuring timing can be determined only by time, thereby simplifying the measurement.

While the invention has been described with reference to preferred embodiments thereof, many modifications and variations of the present invention are possible in light of the above teachings. It is therefore to be understood that within the scope of the appended claims, the invention may be practiced otherwise than as specifically described.

What is claimed is:

1. A method of inspecting a piezoelectric ceramic device comprising the steps of:

heating and increasing the temperature of a piezoelectric ceramic device;

measuring at least one of the piezoelectric phase characteristic and the impedance characteristic of the piezoelectric ceramic device when the piezoelectric ceramic device is at the increased temperature;

comparing at least one of the piezoelectric phase characteristic and the impedance characteristic, which is measured in the step of measuring, with a standard characteristic; and detecting the presence or absence of an internal defect in the piezoelectric ceramic device, based on results of the step of comparing.

2. A method of inspecting a piezoelectric ceramic device according to claim 1, wherein the increased temperature in said step of heating and increasing the temperature is in the vicinity of the maximum temperature in which the piezoelectric characteristic of the piezoelectric device returns to substantially the same characteristic that existed before the piezoelectric device was heated when the piezoelectric device is heated for increasing the temperature and is made to return it to the normal temperature.

3. A method of inspecting a piezoelectric ceramic device according to claim 1, wherein the phase characteristic to be measured is a maximum phase angle $\theta_{max}$.

4. A method of inspecting a piezoelectric ceramic device according to claim 2, wherein the phase characteristic to be measured is a maximum phase angle $\theta_{max}$.

5. A method of inspecting a piezoelectric ceramic device according to claim 1, wherein the impedance characteristic to be measured is a difference Za–Zr between the anti-resonance impedance Za and the resonance impedance Zr of the piezoelectric ceramic device.

6. A method of inspecting a piezoelectric ceramic device according to claim 2, wherein the impedance characteristic to be measured is a difference Za–Zr between the anti-resonance impedance Za and the resonance impedance Zr of the piezoelectric ceramic device.

7. A method of inspecting a piezoelectric ceramic device according to claim 1, wherein in the steps of heating and increasing the temperature, a high frequency measurement signal having a level that is higher than the rated level of the piezoelectric ceramic device is applied to the piezoelectric ceramic device, with the piezoelectric ceramic device being dielectric-heated via the application of the high frequency signal in the step of measuring, said at least one of the phase characteristic and the impedance characteristic of the piezoelectric ceramic device in accordance with the application of the high frequency signal is measured.

8. A method of inspecting a piezoelectric ceramic device according to claim 2, wherein in the steps of heating and increasing the temperature, a high frequency measurement signal having a level that is higher than the rated level of the piezoelectric ceramic device is applied to the piezoelectric ceramic device, with the piezoelectric ceramic device being dielectric-heated via the application of the high frequency signal in the step of measuring, said at least one of the phase characteristic and the impedance characteristic of the piezoelectric ceramic device in accordance with the application of the high frequency signal is measured.

9. A method of inspecting a piezoelectric ceramic device according to claim 3, wherein in the steps of heating and increasing the temperature, a high frequency measurement signal having a level that is higher than the rated level of the piezoelectric ceramic device is applied to the piezoelectric ceramic device, with the piezoelectric ceramic device being dielectric-heated via the application of the high frequency signal in the step of measuring, said at least one of the phase characteristic and the impedance characteristic of the piezoelectric ceramic device in accordance with the application of the high frequency signal is measured.

10. A method of inspecting a piezoelectric ceramic device according to claim 4, wherein in the steps of heating and increasing the temperature, a high frequency measurement signal having a level that is higher than the rated level of the piezoelectric ceramic device is applied to the piezoelectric ceramic device, with the piezoelectric ceramic device being dielectric-heated via the application of the high frequency signal in the step of measuring, said at least one of the phase characteristic and the impedance characteristic of the piezoelectric ceramic device in accordance with the application of the high frequency signal is measured.

11. A method of inspecting a piezoelectric ceramic device according to claim 1, wherein in the step of heating and increasing the temperature, a high frequency inspection signal which is higher than a standard level of the piezoelectric device is applied, due to the application of this high frequency signal, the piezoelectric ceramic device itself is dielectric heated, at the same time, the piezoelectric ceramic device is heated from outside;

in the step of measuring, said at least one of the phase characteristic and the impedance characteristic of the piezoelectric device in accordance with the application of the high frequency signal is measured.

12. A method of inspecting a piezoelectric ceramic device according to claim 2, wherein in the step of heating and increasing the temperature, a high frequency inspection signal which is higher than a standard level of the piezoelectric device is applied, due to the application of this high frequency signal, the piezoelectric ceramic device itself is dielectric heated, at the same time, the piezoelectric ceramic device is heated from outside;

in the step of measuring, said at least one of the phase characteristic and the impedance characteristic of the piezoelectric device in accordance with the application of the high frequency signal is measured.

13. A method of inspecting a piezoelectric ceramic device according to claim 3, wherein in the step of heating and increasing the temperature, a high frequency inspection signal which is higher than a standard level of the piezoelectric device is applied, due to the application of this high frequency signal, the piezoelectric ceramic device itself is dielectric heated, at the same time, the piezoelectric ceramic device is heated from outside;

in the step of measuring, said at least one of the phase characteristic and the impedance characteristic of the piezoelectric device in accordance with the application of the high frequency signal is measured.

14. A method of inspecting a piezoelectric ceramic device according to claim 4, wherein in the step of heating and increasing the temperature, a high frequency inspection signal which is higher than a standard level of the piezoelectric device is applied, due to the application of this high frequency signal, the piezoelectric ceramic device itself is dielectric heated, at the same time, the piezoelectric ceramic device is heated from outside;

in the step of measuring, said at least one of the phase characteristic and the impedance characteristic of the piezoelectric device in accordance with the application of the high frequency signal is measured.

15. A method of inspecting a piezoelectric ceramic device according to claim 1, wherein in the step of measuring, said at least one of the phase characteristic and the impedance characteristic of the piezoelectric ceramic device is measured in different temperature values in the piezoelectric ceramic device.

16. A method of inspecting a piezoelectric ceramic device according to claim 2, wherein in the step of measuring, said at least one of the phase characteristic and the impedance characteristic of the piezoelectric ceramic device is measured in different temperature values in the piezoelectric ceramic device.

17. A method of inspecting a piezoelectric ceramic device according to claim 3, wherein in the step of measuring, said at least one of the phase characteristic and the impedance characteristic of the piezoelectric ceramic device is measured in different temperature values in the piezoelectric ceramic device.

18. A method of inspecting a piezoelectric ceramic device according to claim 1, wherein in said step of measuring, said at least one of the phase characteristic and the impedance characteristic of the piezoelectric ceramic device is measured at plurality of lapse times after the application of the high frequency signal which is higher than the standard level.

19. A method of inspecting a piezoelectric ceramic device according to claim 2, wherein in said step of measuring, said at least one of the phase characteristic and the impedance characteristic of the piezoelectric ceramic device is measured at plurality of lapse times after the application of the high frequency signal which is higher than the standard level.

20. A method of inspecting a piezoelectric ceramic device according to claim 3, wherein in said step of measuring, said at least one of the phase characteristic and the impedance characteristic of the piezoelectric ceramic device is measured at plurality of lapse times after the application of the high frequency signal which is higher than the standard level.

* * * * *